United States Patent [19]

Lee

[11] 4,296,881
[45] Oct. 27, 1981

[54] SURGICAL STAPLER USING CARTRIDGE

[76] Inventor: Sukoo Lee, 30 Widewaters La., Pittsford, N.Y. 14534

[21] Appl. No.: 136,785

[22] Filed: Apr. 3, 1980

[51] Int. Cl.³ .................. B27F 7/00; A61B 17/04
[52] U.S. Cl. ......................... 227/30; 227/DIG. 1; 227/19; 227/110; 128/334 R
[58] Field of Search .............. 128/334 R, 335, 337; 227/DIG. 1, 19, 124, 30, 135, 110, 138, DIG. 1 A, DIG. 1 B, DIG. 1 C

[56] References Cited

U.S. PATENT DOCUMENTS

| | | | |
|---|---|---|---|
| 3,269,630 | 8/1966 | Fleischer | 227/19 X |
| 3,275,211 | 9/1966 | Hirsch et al. | 227/19 |
| 4,047,654 | 9/1977 | Alvarado | 227/DIG. 1 X |

FOREIGN PATENT DOCUMENTS 1276239  6/1972  United Kingdom ............ 128/334 R

*Primary Examiner*—Robert Peshock
*Assistant Examiner*—Mickey Yu

*Attorney, Agent, or Firm*—Stonebraker, Shepard & Stephens

[57] ABSTRACT

A surgical stapling tool 10 using disposable cartridge elements includes an actuator 13 that moves toward and away from a staple folding anvil 20, a holder 22 for an array of staples oriented toward anvil 20, staples and a pusher 23 for pushing staples from holder 22 through tissue 30 and against anvil 20. Pusher 23 is shaped relative to actuator 13 to mount on the actuator in a retention fit and move with the actuator toward anvil 20. Holder 22 is shaped for a retention fit on pusher 23 to move with the pusher independently of the actuator and anvil. Actuator 13 advances pusher 23 and holder 22 until the holder is pressed against tissue 30 and stops. Then further advance of the actuator overcomes a predetermined frictional resistance between the pusher and holder, forces the pusher into the holder, and drives the staples through tissue 30 and against anvil 20 to accomplish the stapling. This eliminates clamping the staple holder against the tissue and avoids damaging the tissue from overclamping.

6 Claims, 6 Drawing Figures

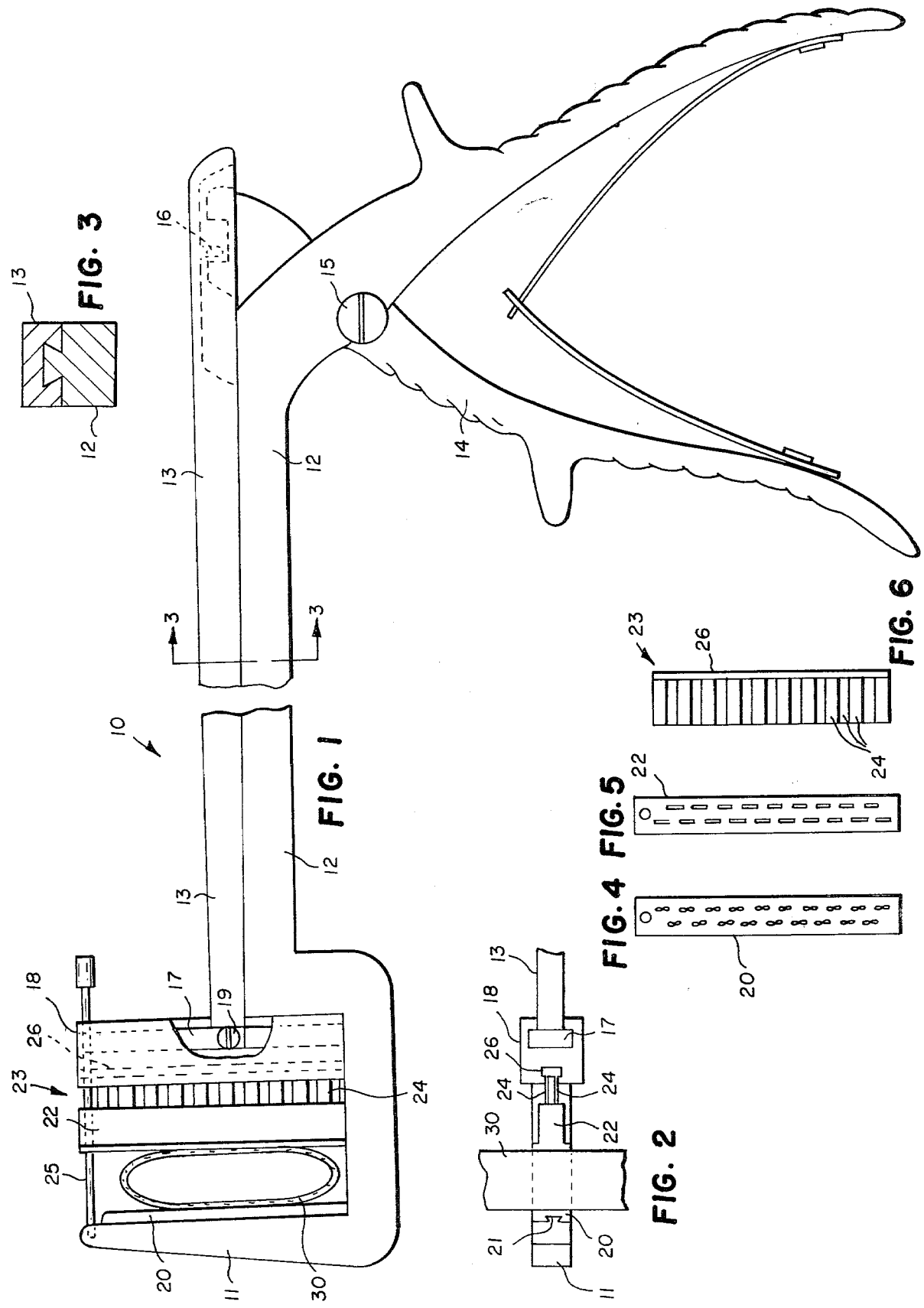

SURGICAL STAPLER USING CARTRIDGE

BACKGROUND

This invention improves on surgical staplers using disposable cartridge elements. It recognizes a way of both simplifying and automating a surgical stapler so that it is easier to use, achieves reliable results, is cheaper to make, is faster to operate, requires less judgment to use, and does not damage the tissue being stapled.

SUMMARY OF THE INVENTION

My surgical stapling tool uses disposable cartridge elements and includes a staple folding anvil, an actuator that moves toward and away from the anvil, a holder with an array of staples oriented toward the anvil, and a pusher that pushes the staples from the holder through the tissue and against the anvil. The actuator and staple pusher are shaped relative to each other so the pusher mounts in a retention fit on the actuator to move toward the anvil. The staple holder mounts in a retention fit on the pusher to move with the pusher independently of the actuator and the anvil. The pusher moves relative to the holder by force that overcomes a predetermined frictional resistance between the two parts. The actuator moves far enough to advance the pusher and holder until the holder presses against and is stopped by the tissue supported by the anvil, and then the pusher continues to advance into the holder to drive the staples through the tissue and against the anvil to staple the tissue. This eliminates clamping the staple holder against the tissue and avoids damaging the tissue from overclamping

DRAWINGS

FIG. 1 is a partially cutaway, side elevational view of a preferred embodiment of my stapler;

FIG. 2 is a fragmentary top view of the stapler of FIG. 1 with the alignment pin removed;

FIG. 3 is a cross-sectional view of the stapler of FIG. 1 taken along the line 3—3 thereof;

FIG. 4 is a front elevational view of a staple folding pad for use in the stapler of FIG. 1;

FIG. 5 is a front elevational view of a staple holder for use in the stapler of FIG. 1; and FIG. 6 is a side elevational view of a staple pusher for use in the stapler of FIG. 1.

DETAILED DESCRIPTION

Stapler 10 as shown in the drawings is used primarily for stapling tubular tissue closed, and it replaces a more complex surgical stapler for the same purpose. The prior art stapler has a fixed jaw holding a staple folding anvil and a movable jaw carrying a staple holder cartridge loaded with staples to be driven through tissue and folded against the anvil. An adjustment screw with a wing nut grip advances the movable jaw to press the staple holder against the tissue supported by the anvil in preparation for stapling, and a gauge along the side of the tool helps the surgeon make this clamping adjustment. Then operation of the stapler pliers moves an actuator that drives a staple pusher into the holder to drive the staples through the clamped tissue and against the anvil. An alignment pin passes through the anvil, staple holder, and tool jaws to insure proper alignment. After each stapling, the wing screw is retracted to open the tool jaws; the alignment pin is removed; and the pin, anvil folding pad, staple holder cartridge, and staple pusher are discarded.

Surgeons often overtighten the wing screw that clamps the staple holder aginst the tissue and later find that they have damaged the tissue by overclamping. In spite of the gauge on the side of the tool, surgeons have a human tendency to overtighten slightly to be sure the staples are well-seated and folded.

I have found a way to eliminate clamping the staple holder against the tissue to be stapled and achieve more reliable stapling without damaging the tissue being stapled. My improvements eliminate the wing screw for clamping the staple holder and save time by eliminating the clamping operation. My simplified tool is cheaper to make and less costly to clean and maintain, and it staples faster and more reliably by automatically pressing the staple holder properly against the tissue being stapled.

Stapler 10 and its associated components as shown in the drawings are one preferred embodiment of my improved tool, and many alternatives are possible. Like previous staplers, it can be made in different sizes and adapted to different surgical stapling tasks. First, the structural details will be described; then the operating principles will be explained.

Stapler 10 includes a fixed anvil jaw 11, a support arm 12, and a movable actuator 13 that slides back and forth along support arm 12 in a sliding fit such as the dove tail guide shown in FIG. 3. Pliers 14 that turn on a pivot screw 15 engage a projection 16 to move actuator 13 back and forth.

The forward end of actuator 13 is formed with a right angle bar 17 parallel with anvil jaw 11. A coupler 18 is slotted to slide over bar 17 and fit on the forward end of actuator 13 where it is held in place by screw 19. Coupler 18 then moves with actuator 13 toward and away from anvil jaw 11 and can be removed from actuator 13 for cleaning. With coupler 18 removed, actuator 13 can be slid off of support arm 12; and with removal of pivot screw 15, pliers 14 separate so that tool 10 easily disassembles for cleaning.

The stapling is accomplished by disposable cartridge elements mounted on tool 10. These include a staple folding pad 20 mounted on a slide 21 on anvil jaw 11, a staple holder 22 loaded with an array of staples, and a staple pusher 23 having pusher bars 24 that fit into slots in staple holder 22 to push the staples out of holder 22 at the proper time. A disposable alignment pin 25 fits through aligned holes in jaw 11, anvil pad 20, holder 22, and coupler 18 to insure vertical alignment between these elements.

Pusher 23 has an anchoring head 26 that fits in a receiving slot on coupler 18 to mount pusher 23 in a retention fit on coupler 18. Pusher 23 is then fixed relative to both coupler 18 and actuator 13 and moves back and forth with actuator 13.

Instead of staple holder 22 being held by a clamping jaw, holder 22 is shaped for a retention fit on pusher 23 were it moves along with pusher 23 independently of actuator 13 or anvil jaw 11. Pusher 23 is movable relative to holder 22 and has a predetermined frictional resistance to movement within holder 22. Pusher 23 and holder 22 are dimensioned so that holder 22 will not readily slip off the free ends of staple pusher bars 24; but when sufficient force is applied to overcome the frictional resistance, bars 24 will slide more deeply into holder 22 and push the staple array out the front of holder 22 and into the tissue to be stapled.

To operate, tool 10 is assembled as illustrated; and disposable cartridge elements 20, 22, and 23 are mounted as previously described; tissue 30 to be stapled is positioned between anvil 20 and staple holder 22; and alignment pin 25 is inserted through the stapler jaws and the cartridge elements to insure vertical alignment. Then the surgeon merely squeezes pliers 14 to move actuator 13 toward anvil jaw 11 and the stapling of tissue 30 is automatically and reliably completed.

As actuator 13, coupler 18, and pusher 23 move toward anvil jaw 11, pusher 23 carries staple holder 22 into compressed engagement with tissue 30, which is supported by anvil pad 20. Holder 22 stops when it is firmly and adequately pressed against tissue 30 at the limit of its frictional resistance on pusher 23. Continued advance of pusher 23 beyond this point overcomes the frictional resistance between pusher 23 and holder 22 and forces pusher bars 24 into holder 22. This drives all the staples of the staple array out of the forward end of holder 22, through compressed tissue 30, and against staple folding anvil 20 which folds the staples in place.

Eliminating a wing screw to clamp the staple holder against tissue 30 not only simplifies tool 10 and eliminates the time-consuming clamping operation, but it also eliminates the judgment required for proper clamping tension and prevents excessive clamping pressure that damages tissue 30. With my tool, as soon as holder 22 is pressed snugly against tissue 30, pusher 23 begins advancing into holder 22 to drive the staples through tissue 30. Furthermore, my tool operates much faster by eliminating the clamping step and requiring only that the surgeon operate pliers 14 after setting up the tool.

Proper compression of holder 22 against tissue 30 is accomplished by designing the fit between pusher 23 and holder 22 so that the desired amount of pressure occurs as the frictional engagement between pusher 23 and holder 22 is overcome. This can be accomplished by choosing the proper parameters for the fit of the staples in holder 22 and the fit of pusher bars 24 within the slots in holder 22.

Although the illustrated configuration of tool 10 and associated cartridge components is preferred for simplicity and effectiveness, there are many other ways that an actuator can be moved and can be shaped or provided with a coupler for holding a pusher carrying a staple holder. Also, staple arrays and configurations of holders, folding pads, alignment pins, and other details can all be varied within the scope of the invention.

I claim:

1. A surgical stapling tool using disposable cartridge elements and having a staple folding anvil, an actuator movable toward and away from said anvil, a holder for an array of staples oriented toward said anvil, and a pusher for pushing said staples from said holder through tissue to be stapled and against said anvil, said tool comprising:
   a. said movable actuator and said staple pusher being shaped relative to each other so said pusher mounts on said actuator in a retention fit and moves with said actuator toward said anvil;
   b. said holder being shaped for a retention fit on said pusher for movement with said pusher independently of said actuator and said anvil;
   c. said pusher being movable relative to said holder by force overcoming a predetermined frictional resistance between said pusher and said holder; and
   d. said actuator being movable through a distance sufficient to advance said pusher and said holder until said holder presses against and is stopped by tissue supported by said anvil and then continuing to advance said pusher into said holder to drive said staples through said tissue and against said anvil to staple said tissue.

2. The tool of claim 1 wherein said pusher has an anchoring head and said actuator has a slot shaped to receive said head.

3. The tool of claim 1 wherein said actuator has a removable coupler shaped to hold said pusher.

4. The tool of claim 3 wherein said pusher has an anchoring head and said actuator has a slot shaped to receive said head.

5. The tool of claim 4 wherein said actuator has a cross bar and said coupler has a slot that fits said cross bar to mount said coupler on said actuator.

6. The tool of claim 5 wherein said actuator is slidably mounted on said tool and is removable from said tool after removal of said coupler from said actuator.

* * * * *